(12) United States Patent
Wadamoto et al.

(10) Patent No.: US 8,563,786 B2
(45) Date of Patent: Oct. 22, 2013

(54) METHOD FOR PRODUCING OPTICALLY ACTIVE ALCOHOL

(75) Inventors: Manabu Wadamoto, Fujisawa (JP); Kazuhiko Yoshinaga, Ichihara (JP); Takushi Nagata, Yokohama (JP); Seayad Abdul Majeed, Singapore (SG); Ramalingam Balamurugan, Singapore (SG); Chai Christina L. L., Singapore (SG)

(73) Assignees: Mitsui Chemicals, Inc., Minato-Ku, Tokyo (JP); Agency for Science, Technology and Research, Connexis (SG)

( * ) Notice: Subject to any disclaimer, the term of this patent is extended or adjusted under 35 U.S.C. 154(b) by 145 days.

(21) Appl. No.: 13/258,735

(22) PCT Filed: Mar. 26, 2010

(86) PCT No.: PCT/JP2010/002181
§ 371 (c)(1),
(2), (4) Date: Nov. 30, 2011

(87) PCT Pub. No.: WO2010/109901
PCT Pub. Date: Sep. 30, 2010

(65) Prior Publication Data
US 2012/0088938 A1   Apr. 12, 2012

(30) Foreign Application Priority Data

Mar. 27, 2009   (JP) .................................. 2009-079953

(51) Int. Cl.
C07C 27/18   (2006.01)

(52) U.S. Cl.
USPC ............ 568/878; 568/716; 568/840; 568/876

(58) Field of Classification Search
None
See application file for complete search history.

(56) References Cited

U.S. PATENT DOCUMENTS 4,508,926 A   4/1985   Toth et al.
7,592,487 B2 *   9/2009   Chan et al. .................... 564/337

FOREIGN PATENT DOCUMENTS

| JP | 59-134740 A | 8/1984 |
|---|---|---|
| JP | 9-235255 A | 9/1997 |
| JP | 2002-020334 A | 1/2002 |
| JP | 2002-332252 A | 11/2002 |
| WO | WO 2005/087707 A1 | 9/2005 |

OTHER PUBLICATIONS

Wu et al., "Remarkably Efficient Enantioselective Titanium(IV)-(R)-H-BINOLate Catalyst for Arylations to Aldehydes by Triaryl(tetrahydrofuran)aluminum Reagents", Journal of the American Chemical Society, Nov. 2006, pp. 14808-14809, vol. 128. No. 46.
Weber et al., "Ti-TADDOLate-Catalyzed, Highly Enantioselective Addition of Alkyl- and Aryl-Titanium Derivatives to Aldehydes", Tetrahedron, 1994, pp. 7473-7484, vol. 50, No. 25.
Muramatsu et al., "Catalytic Asymmetric Alkylation of Aldehydes with Grignard Reagents", Angew. Chem. Int. Ed., 2008, pp. 1088-1090, vol. 47.
Seebach et al., "Enantioselektive Addition von Arylgruppen an aromatische Aldehyde mit Aryltitan-Binaphthol-Derivaten", Chem. Ber., 1985, pp. 3676-3685, vol. 118.
Tanigawa et al., Catalytic Asymmetric Alkylation of Aldehydes with Grignard Reagents, 88th Annual Meeting of Chem. Soc. of Japan, 2008, pp. 1569 (with English translation).
International Search Report (PCT/ISA/210) issued on Jun. 1, 2010, by Japanese Patent Office as the International Searching Authority for International Application No. PCT/JP2010/002181.
Muramatsu, Y. et al., "Catalytic Asymmetric Aryl Transfer Reactions to Aldehydes With Grignard Reagents as the Aryl Source", Chem. Eur. J., vol. 14, pp. 10560-10563 (Dec. 13, 2008) XP-002683790.
Extended European Search Report dated Oct. 1, 2012, issued in corresponding European Patent Application No. 10755703.5-1211 / 2412694. (5 pages).

* cited by examiner

*Primary Examiner* — Sudhakar Katakam
(74) *Attorney, Agent, or Firm* — Buchanan Ingersoll & Rooney PC

(57) ABSTRACT

Disclosed is a method for producing an optically active alcohol including reacting a titanium compound, an aromatic magnesium compound and a carbonyl compound in the presence of an optically active biphenol compound having a predetermined structure and an ether compound having a predetermined structure.

13 Claims, No Drawings

METHOD FOR PRODUCING OPTICALLY ACTIVE ALCOHOL

TECHNICAL FIELD

The present invention relates to a method for producing an optically active alcohol.

BACKGROUND ART

As a method for producing an optically active benzhydrol, which is one of optically active alcohols, a lot of cases have already been reported. For example, there has been a known method of conducting an asymmetric reduction of asymmetrical benzophenones, and typical examples are as follows.

(1) Patent Document 1 discloses a method of conducting an asymmetric hydrogenation reaction of asymmetrical benzophenones using an optically active ruthenium complex as a catalyst.

(2) Patent Document 2 discloses a method of conducting an asymmetric reduction of asymmetrical benzophenones with sodium borohydride using an optically active cobalt complex as a catalyst.

However, in these methods, when a substituent is not present at the ortho position of at least one aromatic ring of raw material asymmetrical benzophenones, it has been impossible to produce benzhydrols having a high optical purity, and the substrate generality has been poor.

Meanwhile, as a method for producing an optically active benzhydrol from an aromatic aldehyde and an aryl metal compound, some cases have been known.

(3) Patent Document 3 discloses a method of reacting a diaryl zinc compound with an aromatic aldehyde in the presence of a catalytic amount of an optically active amino alcohol.

(4) Non-Patent Document 1 discloses a method of reacting a triarylaluminum compound with an aromatic aldehyde in the presence of tetra-iso-propoxy titanium and a catalytic amount of an optically active biphenol compound.

(5) Non-Patent Document 2 discloses a method of reacting an aryltitanium compound with an aromatic aldehyde in the presence of a catalytic amount of an optically active Tadol titanium complex.

(6) Non-Patent Document 3 discloses a method of reacting an arylmagnesium compound with an aromatic aldehyde in the presence of a tetra-iso-propoxy titanium compound and a catalytic amount of an optically active binaphthyl compound.

(7) Non-Patent Document 4 discloses a method of reacting an optically active aryltitanium compound derived from an optically active binaphthol with an aromatic aldehyde.

In the methods of (3) and (4), an aryl metal compound in an excessive amount relative to the aldehyde is needed, which is not practical particularly when addition of a complex aromatic compound is desired. Furthermore, these aryl metal compounds are highly reactive and unstable, but in order to achieve high enantioselectivity, the aryl metal compound needs to be isolated. In the method (5), in order to carry out the reaction using an aryltitanium compound, the amount of the aryltitanium compound is close to 1 equivalent relative to the aldehyde and the reaction proceeds quantitatively. However, the aryltitanium compound needs to be isolated, and in order to achieve high enantioselectivity, the reaction temperature needs to be a lower temperature. In the method (6), a large excess amount (5.8 equivalents) of tetra-iso-propoxy titanium is needed. Furthermore, with regard to synthesis of benzhydrols, enantioselectivity is not sufficient either. In the method (7), equal to or more than 1 equivalent of an optically active binaphthol is needed.

As described above, a method for producing an optically active alcohol combined with industrially desirable conditions, particularly an optically active benzhydrol, has not been known.

RELATED DOCUMENT

Patent Document

Patent Document 1: Japanese Laid-open Patent Publication No. 1997-235255
Patent Document 2: Japanese Laid-open Patent Publication No. 2002-332252
Patent Document 3: International Publication Pamphlet No. 2005/087707
Non-Patent Document 1: J. Am. Chem. Soc., vol. 128, p. 14808 (2006)
Non-Patent Document 2: Tetrahedron, vol. 50, p. 7473 (1994)
Non-Patent Document 3: Angew. Chem. Int. Ed., vol. 47, p. 1088 (2008)
Non-Patent Document 4: Chem. Ber., vol. 118, p. 3673 (1985)

DISCLOSURE OF THE INVENTION

An object of the present invention is to provide a method for producing an optically active alcohol which is industrially advantageous, particularly an optically active benzhydrol.

In order to solve the above objects, the present inventors have conducted an extensive study and as a result, have found that an optically active alcohol having a high optical purity is obtained from a titanium compound, an aromatic magnesium compound and a carbonyl compound in the presence of an optically active biphenol compound and an ether compound. Furthermore, they have conducted an extensive study and as a result, the present invention has been completed.

That is, the present invention includes the following inventions.

[1] A method for producing an optically active alcohol including reacting a titanium compound represented by the following general formula (1), an aromatic magnesium compound represented by the following general formula (4) and a carbonyl compound in the presence of an optically active biphenol compound represented by the following general formula (2) and an ether compound represented by the following general formula (3),

[Chemical Formula 1]

$$Ti(OR^a)_m X_{(4-m)} \qquad (1)$$

wherein, in the formula, $R^a$ is an alkyl group, an alkenyl group, an aryl group or an acyl group, which may have a substituent; X is a halogen atom; and m is an integer of 0 to 4,

[Chemical Formula 2]

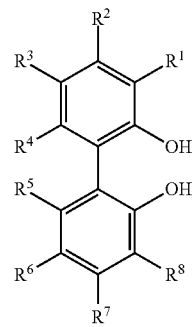

(2)

wherein, in the general formula (2), $R^1$ to $R^8$ are each independently a hydrogen atom, a halogen atom, an alkyl group, an alkenyl group, an alkynyl group, an aryl group, an aromatic heterocyclic group, a non-aromatic heterocyclic group, an acyl group, a carboxyl group, an alkoxycarbonyl group, an aryloxycarbonyl group, a carbamoyl group, a hydroxyl group, an alkoxy group, an aryloxy group, a thiol group, an alkylthio group, an arylthio group, an amino group, an alkylamino group, an arylamino group, a cyano group, a nitro group, a silyl group or a siloxy group, which may have a substituent or may be linked to each other to form a ring,

[Chemical Formula 3]

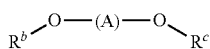

(3)

wherein, in the formula, $R^b$ and $R^c$ are each independently an alkyl group, an alkenyl group or an aryl group, which may have a substituent or may be linked to each other to form a ring; and (A) is a group containing one or more carbon atoms, which connects two oxygen atoms in the formula,

[Chemical Formula 4]

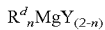

(4)

wherein, in the formula, $R^d$ is an aromatic group, which may have a substituent; Y is a halogen atom; and n is an integer of 1 or 2.

[2] The method for producing an optically active alcohol according to [1], in which the optically active biphenol compound is represented by the following general formula (5),

[Chemical Formula 5]

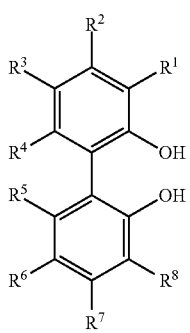

(5)

wherein, in the formula, $R^1$ to $R^8$ are each independently a hydrogen atom, a halogen atom, an alkyl group, an alkenyl group, an alkynyl group, an aryl group, an aromatic heterocyclic group, a non-aromatic heterocyclic group, an acyl group, a carboxyl group, an alkoxycarbonyl group, an aryloxycarbonyl group, a carbamoyl group, a hydroxyl group, an alkoxy group, an aryloxy group, a thiol group, an alkylthio group, an arylthio group, an amino group, an alkylamino group, an arylamino group, a cyano group, a nitro group, a silyl group or a siloxy group, which may have a substituent or may be linked to each other to form a ring; and at least one of $R^4$ and $R^5$ is not a hydrogen atom.

[3] The method for producing an optically active alcohol according to [1] or [2], in which the optically active biphenol compound is represented by the following general formula (6),

[Chemical Formula 6]

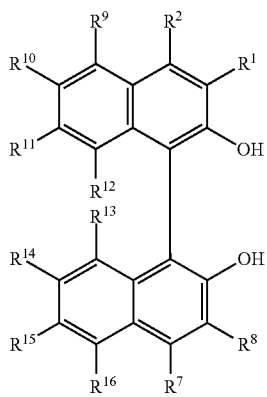

(6)

wherein, in the formula, $R^1$, $R^2$, $R^7$, $R^8$, and $R^9$ to $R^{16}$ are each independently a hydrogen atom, a halogen atom, an alkyl group, an alkenyl group, an alkynyl group, an aryl group, an aromatic heterocyclic group, a non-aromatic heterocyclic group, an acyl group, a carboxyl group, an alkoxycarbonyl group, an aryloxycarbonyl group, a carbamoyl group, a hydroxyl group, an alkoxy group, an aryloxy group, a thiol group, an alkylthio group, an arylthio group, an amino group, an alkylamino group, an arylamino group, a cyano group, a nitro group, a silyl group or a siloxy group, which may have a substituent or may be linked to each other to form a ring.

[4] The method for producing an optically active alcohol according to [3], in which the optically active biphenol compound is the following formula (7),

[Chemical Formula 7]

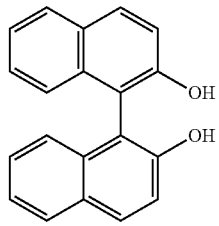

(7)

[5] The method for producing an optically active alcohol according to [1] or [2], in which the optically active biphenol compound is represented by the following general formula (8),

[Chemical Formula 8]

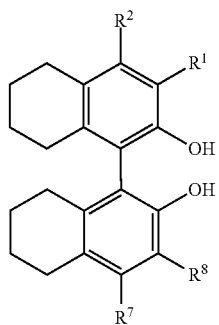

(8)

wherein, in the formula, $R^1$, $R^2$, $R^7$ and $R^8$ are each independently a hydrogen atom, a halogen atom, an alkyl group, an alkenyl group, an alkynyl group, an aryl group, an aromatic heterocyclic group, a non-aromatic heterocyclic group, an acyl group, a carboxyl group, an alkoxycarbonyl group, an aryloxycarbonyl group, a carbamoyl group, a hydroxyl group, an alkoxy group, an aryloxy group, a thiol group, an alkylthio group, an arylthio group, an amino group, an alkylamino group, an arylamino group, a cyano group, a nitro group, a silyl group or a siloxy group, which may have a substituent or may be linked to each other to form a ring.

[6] The method for producing an optically active alcohol according to [5], in which the optically active biphenol compound is the following formula (9),

[Chemical Formula 9]

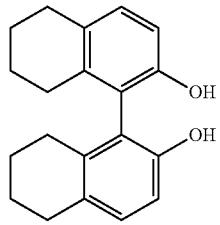

(9)

[7] The method for producing an optically active alcohol according to any one of [1] to [6], in which the amount of the ether compound is equal to or more than 10 equivalents, relative to the aromatic magnesium compound.

[8] The method for producing an optically active alcohol according to any one of [1] to [7], in which the ether compound is dioxane.

[9] The method for producing an optically active alcohol according to any one of [1] to [8], in which the titanium compound is represented by the following general formula (10),

[Chemical Formula 10]

$$Ti(OR^a)_m X_{(4-m)} \quad (10)$$

wherein, in the formula, $R^a$ is an alkyl group, an alkenyl group, an aryl group or an acyl group, which may have a substituent; X is a halogen atom; and m is an integer of 0 to 3.

[10] The method for producing an optically active alcohol according to any one of [1] to [9], in which the amount of the optically active biphenol compound is equal to or more than 0.1 mole % and equal to or less than 50 mole %, based on 100 mole % of the carbonyl compound.

[11] The method for producing an optically active alcohol according to any one of [1] to [10], in which the amount of the titanium compound is equal to or more than 50 mole % and equal to or less than 300 mole %, based on 100 mole % of the carbonyl compound.

[12] The method for producing an optically active alcohol according to any one of [1] to [11], in which the carbonyl compound is aldehyde represented by the following general formula (11),

[Chemical Formula 11]

(11)

wherein, in the formula, $R^e$ is an alkyl group, an alkenyl group, an alkynyl group, an aryl group, an aromatic heterocyclic group or a non-aromatic heterocyclic group.

[13] The method for producing an optically active alcohol according to [12], in which the aldehyde is an aromatic aldehyde.

EFFECT OF THE INVENTION

According to the present invention, an optically active alcohol having a high optical purity is produced at a high efficiency, as compared to the conventional method.

DESCRIPTION OF EMBODIMENTS

The present invention will be described in more detail below.

(1) Titanium Compound

In the present invention, there is used a titanium compound represented by the following general formula (1),

[Chemical Formula 12]

$$Ti(OR^a)_m X_{(4-m)} \quad (1)$$

wherein, in the general formula (1), $R^a$ is an alkyl group, an alkenyl group, an aryl group or an acyl group, which may have a substituent.

The structure of the alkyl group in $R^a$ is not particularly limited, but preferably used is a linear, branched or cyclic alkyl group having equal to or less than 20 carbon atoms. Examples of the linear alkyl group include a methyl group, an ethyl group, an n-propyl group, an n-butyl group, an n-pentyl group, an n-hexyl group, an n-heptyl group, an n-octyl group, an n-nonyl group, an n-decyl group and the like. Examples of the branched alkyl group include an iso-propyl group, an iso-butyl group, a sec-butyl group, a tert-butyl group and the like. Examples of the cyclic alkyl group include a cyclopropyl group, a cyclobutyl group, a cyclopentyl group, a cyclohexyl group, a cycloheptyl group, a cyclooctyl group and the like. The structure of the alkenyl group in $R^a$ is not particularly limited, but preferably used is a linear, branched or cyclic alkenyl group having equal to or less than 20 carbon atoms. Concrete examples include a vinyl group, an allyl group, a 1-propenyl group and the like. The structure of the aryl group in $R^a$ is not particularly limited, but preferably used is an aryl group having equal to or less than 22 carbon atoms. Concrete examples include a phenyl group, a naphthyl group, an anthryl group and the like. The structure of the acyl group in $R^a$ is not particularly limited, but preferably used is an acyl group having equal to or less than 20 carbon atoms. Concrete examples include an alkylcarbonyl group such as a formyl group, an acetyl group or the like; and an arylcarbonyl group such as a benzoyl group, a naphthoyl group, an anthrylcarbonyl or the like.

The kind of the substituent on $R^a$ is not particularly limited, and examples include a halogen atom, an alkyl group, an alkenyl group, an alkynyl group, an aryl group, an aromatic heterocyclic group, a non-aromatic heterocyclic group, an acyl group, a carboxyl group, an alkoxycarbonyl group, an aryloxycarbonyl group, a carbamoyl group, a hydroxyl group, an alkoxy group, an aryloxy group, a thiol group, an alkylthio group, an arylthio group, an amino group, an alkylamino group, an arylamino group, a cyano group, a nitro group, a silyl group, a siloxy group and the like.

X in the general formula (1) is not particularly limited so long as it is a halogen atom. Examples of the halogen atom include a fluorine atom, a chlorine atom, a bromine atom, an iodine atom and the like.

In general formula (1), m is an integer not less than 0 and not more than 4. Concrete examples of the titanium compound include tetramethoxy titanium, tetraethoxy titanium, tetra-n-propoxy titanium, tetra-iso-propoxy titanium, tetra-n-butoxy titanium, tetra-2-ethylhexoxy titanium, di-iso-propoxy bis(acetylacetonato)titanium, chloro-tri-iso-propoxy titanium, dichloro-di-iso-propoxy titanium, titanium tetrachloride and the like.

As the above titanium compound, it is preferable that $R^a$ is an alkyl group having equal to or more than 2 and equal to or less than 10 carbon atoms, X is a chlorine atom or a bromine atom, and m is an integer not less than 0 and not more than 3, and it is more preferable that $R^a$ is an alkyl group having equal to or more than 2 and equal to or less than 4 carbon atoms, X is a chlorine atom, and m is an integer not less than 2 and not more than 3. Preferable Examples of such titanium compounds include chloro-tri-iso-propoxy titanium, dichloro-di-iso-propoxy titanium and titanium tetrachloride, and more preferable examples include chloro-tri-iso-propoxy titanium and dichloro-di-iso-propoxy titanium. These titanium compounds may be used singly or in combination of two or more kinds.

These titanium compounds are produced in accordance with a known method. For example, a titanium compound can be produced according to a known method as disclosed in European Patent Publication No. 0641762 (for example, pp. 13 and 14) or the like. According to other known methods, for example, a solution containing chloro-tri-iso-propoxy titanium can be produced by reacting 3 equivalents of tetra-iso-propoxy titanium and 1 equivalent of titanium tetrachloride in a solvent. The aforementioned prepared solution containing a titanium compound can be supplied for the present invention as it is, so long as a solvent suitable for the present invention is selected as a solvent. Furthermore, the titanium compound is purified and isolated from the aforementioned prepared solution containing a titanium compound according to a known method, and then it is also supplied for the present invention.

The amount of the aforementioned titanium compound is not particularly limited, but it is preferably equal to or more than 50 mole % and equal to or less than 300 mole %, based on 100 mole % of the carbonyl compound used in the present invention. The amount of the titanium compound is more preferably equal to or more than 75 mole % and equal to or less than 200 mole %. When it is in this range, the amount of titanium waste (for example, titanium dioxide) to be removed after the reaction is reduced and an optically active alcohol having a high optical purity is produced.

(2) Optically Active Biphenol Compound

In the present invention, the reaction is carried out in the presence of an optically active biphenol compound represented by the following general formula (2),

[Chemical Formula 13]

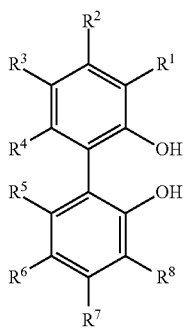

(2)

wherein, in the general formula (2), $R^1$ to $R^8$ are each independently a hydrogen atom, a halogen atom, an alkyl group, an alkenyl group, an alkynyl group, an aryl group, an aromatic heterocyclic group, a non-aromatic heterocyclic group, an acyl group, a carboxyl group, an alkoxycarbonyl group, an aryloxycarbonyl group, a carbamoyl group, a hydroxyl group, an alkoxy group, an aryloxy group, a thiol group, an alkylthio group, an arylthio group, an amino group, an alkylamino group, an arylamino group, a cyano group, a nitro group, a silyl group or a siloxy group, which may have a substituent or may be linked to each other to form a ring; and each of $R^1$ to $R^8$ is preferably a hydrogen atom, an alkyl group, an alkenyl group, an aryl group, a halogen atom and the like.

The halogen atom in $R^1$ to $R^8$ is not particularly limited, and examples include a fluorine atom, a chlorine atom, a bromine atom, an iodine atom and the like. The structure of the alkyl group in $R^1$ to $R^8$ is not particularly limited, but preferably used is a linear, branched or cyclic alkyl group having equal to or less than 20 carbon atoms. Examples of the linear alkyl group include a methyl group, an ethyl group, an n-propyl group, an n-butyl group, an n-pentyl group, an n-hexyl group, an n-heptyl group, an n-octyl group, an n-nonyl group, an n-decyl group and the like. Examples of the branched alkyl group include an iso-propyl group, an iso-butyl group, a sec-butyl group, a tert-butyl group and the like. Examples of the cyclic alkyl group include a cyclopropyl group, a cyclobutyl group, a cyclopentyl group, a cyclohexyl group, a cycloheptyl group, a cyclooctyl group and the like. The structure of the alkenyl group in $R^1$ to $R^8$ is not particularly limited, but preferably used is a linear, branched or cyclic alkenyl group having equal to or less than 20 carbon atoms. Concrete examples include a vinyl group, an allyl group, a 1-propenyl group and the like. The structure of the alkynyl group in $R^1$ to $R^8$ is not particularly limited, but preferably used is a linear, branched or cyclic alkynyl group having equal to or less than 20 carbon atoms. Concrete examples include an ethynyl group, a propargyl group and the like. The structure of the aryl group in $R^1$ to $R^8$ is not particularly limited, but preferably used is an aryl group having equal to or less than 22 carbon atoms. Concrete examples include a phenyl group, a naphthyl group, an anthryl group and the like. The structure of the aromatic heterocyclic group in $R^1$ to $R^8$ is not particularly limited, but preferably used is an aromatic heterocyclic group having equal to or less than 20 carbon atoms. Concrete examples include an imidazolyl group, a furyl group, a thienyl group, a pyridyl group and the like. The structure of the non-aromatic heterocyclic group in $R^1$ to $R^8$ is not particularly limited, but preferably used is a non-aromatic heterocyclic group having equal to or less than 20 carbon atoms. Concrete examples include a pyrrolidinyl group, a piperidyl group, a tetrahydrofuryl group, a tetrahydropyranyl group and the like. The structure of the acyl group in $R^1$ to $R^8$ is not particularly limited, but preferably used is an acyl group having equal to or less than 20 carbon atoms. Concrete examples include an alkylcarbonyl group such as a formyl group, an acetyl group or the like, and an arylcarbonyl group such as a benzoyl group, a naphthoyl group, an anthrylcarbonyl group or the like. The structure of the alkoxycarbonyl group in $R^1$ to $R^8$ is not particularly limited, but preferably used is an alkoxycarbonyl group having equal to or less than 20 carbon atoms. Concrete examples include a methoxycarbonyl group, an ethoxycarbonyl group, an n-propoxycarbonyl group, a tert-butoxycarbonyl group and the like. The structure of the aryloxycarbonyl group in $R^1$ to $R^8$ is not particularly limited, but preferably used is an aryloxycarbonyl group having equal to or less than 20 carbon atoms. Concrete examples include a phenyloxycarbonyl group, a naphthyloxycarbonyl group and the like. The structure of the carbamoyl group in $R^1$ to $R^8$ is not particularly limited, but preferably used is a carbamoyl group having equal to or less than 20 carbon atoms. Concrete examples include an aminocarbonyl group, a methylaminocarbonyl group, a dimethylaminocarbonyl group and the like. The structure of the alkoxy group in $R^1$ to $R^8$ is not particularly limited, but preferably used is an alkoxy group having equal to or less than 20 carbon atoms. Concrete examples include a methoxy group, an ethoxy group, an n-propoxy group, an iso-propoxy group, an n-butoxy group, a tert-butoxy group and the like. The structure of the aryloxy group in $R^1$ to $R^8$ is not particularly limited, but preferably used is an aryloxy group having equal to or less than 20 carbon atoms. Concrete examples include a phenoxy group, a naphthyloxy group and the like. The structure of the alkylthio group in $R^1$ to $R^8$ is not particularly limited, but preferably used is an alkylthio group having equal to or less than 20 carbon atoms. Concrete examples include a methylthio group, an ethylthio group and the like. The structure of the arylthio group in $R^1$ to $R^8$ is not particularly limited, but preferably used is an arylthio group having equal to or less than 20 carbon atoms. Concrete examples include a phenylthio group, a naphthylthio group and the like. The structure of the alkylamino group in $R^1$ to $R^8$ is not particularly limited, but preferably used is an alkylamino group having equal to or less than 20 carbon atoms. Concrete examples include a methylamino group, a dimethylamino group and the like. The structure of the arylamino group in $R^1$ to $R^8$ is not particularly limited, but preferably used is an arylamino group having equal to or less than 20 carbon atoms. Concrete examples include a phenylamino group, a naphthylamino group and the like. The structure of the silyl group in $R^1$ to $R^8$ is not particularly limited, but preferably used is a silyl group having equal to or less than 20 carbon atoms. Concrete examples include a trimethylsilyl group, a triethylsilyl group and the like. The structure of the siloxy group in $R^1$ to $R^8$ is not particularly limited, but preferably used is a siloxy group having equal to or less than 20 carbon atoms. Concrete examples include a trimethylsiloxy group, a triethylsiloxy group and the like.

The kind of the substituent on $R^1$ to $R^8$ is not particularly limited, and examples include a halogen atom, an alkyl group, an alkenyl group, an alkynyl group, an aryl group, an aromatic heterocyclic group, a non-aromatic heterocyclic group, an acyl group, a carboxyl group, an alkoxycarbonyl group, an aryloxycarbonyl group, a carbamoyl group, a hydroxyl group, an alkoxy group, an aryloxy group, a thiol group, an alkylthio group, an arylthio group, an amino group, an alkylamino group, an arylamino group, a cyano group, a nitro group, a silyl group, a siloxy group and the like. Preferable examples of the substituent on $R^1$ to $R^8$ include a hydrogen atom, an alkyl group, an alkenyl group, an aryl group, a halogen atom and the like.

As the optically active biphenol compound, preferably used is an optically active biphenol compound represented by the following general formula (5),

[Chemical Formula 14]

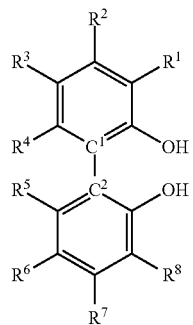

(5)

wherein, in the general formula (5), $R^1$ to $R^8$ are the same as $R^1$ to $R^8$ in the above general formula (2); each of $C^1$ and $C^2$ is a carbon atom, and has an axial asymmetry in the $C^1$—$C^2$ bond; in the optically active biphenol represented by the general formula (5), when other asymmetry is not present, two kinds of enantiomeric isomers, an (R) form and an (S) form, derived from an axial asymmetry in the $C^1$—$C^2$ bond may be present, but both may be used in the present invention.

Herein, "having an axial asymmetry" means that free rotation of the $C^1$—$C^2$ bond is hindered so that two kinds of optical isomers are present.

In the general formula (5), in an optically active biphenol compound in which all of $R^1$ to $R^8$ are each a hydrogen atom, and free rotational energy barrier of an aromatic ring is low, the optically active state is not possibly maintained in the normal conditions (the reaction temperature of the present invention is, for example, equal to or more than −80 degrees centigrade and equal to or less than 100 degrees centigrade or the like).

Accordingly, in the normal conditions (the reaction temperature of the present invention is, for example, equal to or more than −80 degrees centigrade and equal to or less than 100 degrees centigrade or the like), preferably used is an optically active biphenol compound (a biphenol compound with an optical activity maintained) in which free rotation is hindered. From the viewpoint of hindrance of free rotation, it is preferable that at least one of $R^4$ and $R^5$ in the general formula (5) is not a hydrogen atom. In such an optically active biphenol compound, because of the presence of a bulky substituent, free rotation is hindered at a normal reaction temperature and an optical activity is maintained and as a result, an optically active alcohol of the present invention is effectively and stably produced, which is industrially advantageous.

Furthermore, the optically active biphenol compound may be symmetric or asymmetric. From the viewpoint of cost, preferably used is a symmetric optically active biphenol compound. So, it is preferable that, in the general formula (5), at least, both $R^4$ and $R^5$ are not hydrogen atoms.

As the above-mentioned optically active biphenol compound, more preferably used is an optically active biphenol compound represented by the following general formula (6),

[Chemical Formula 15]

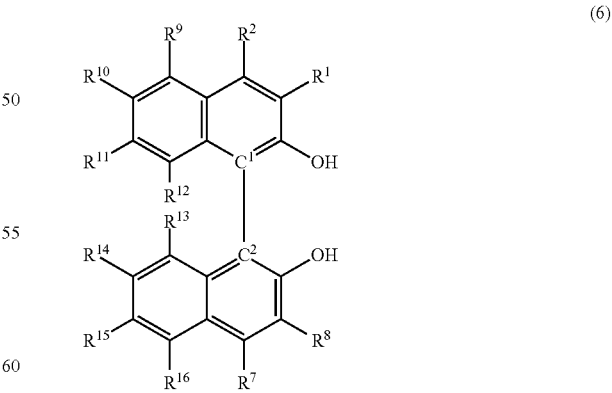

(6)

wherein, in the general formula (6), $R^1$, $R^2$, $R^7$, $R^8$, $C^1$ and $C^2$ are the same as $R^1$, $R^2$, $R^7$, $R^8$, $C^1$ and $C^2$ in the above general formula (5); $R^9$ to $R^{16}$ are each independently a hydrogen atom, a halogen atom, an alkyl group, an alkenyl group, an alkynyl group, an aryl group, an aromatic heterocyclic group, a non-aromatic heterocyclic group, an acyl group, a carboxyl group, an alkoxycarbonyl group, an aryloxycarbonyl group, a carbamoyl group, a hydroxyl group, an alkoxy group, an aryloxy group, a thiol group, an alkylthio group, an arylthio group, an amino group, an alkylamino group, an arylamino group, a cyano group, a nitro group, a silyl group or a siloxy group, which may have a substituent or may be linked to each other to form a ring; and $R^9$ to $R^{16}$ are each preferably a hydrogen atom, an alkyl group, an alkenyl group, an aryl group, a halogen atom or the like; and each of $C^1$ and $C^2$ has an axial asymmetry in the $C^1$—$C^2$ bond under the aforementioned normal conditions.

Concrete examples of the halogen atom in $R^9$ to $R^{16}$ include concrete examples of the halogen atom illustrated in $R^1$ and the like in the above general formula (2). Concrete examples of the alkyl group in $R^9$ to $R^{16}$ include concrete examples of the alkyl group illustrated in $R^1$ and the like in the above general formula (2). Concrete examples of the alkenyl group in $R^9$ to $R^{16}$ include concrete examples of the alkenyl group illustrated in $R^1$ and the like in the above general formula (2). Concrete examples of the alkynyl group in $R^9$ to $R^{16}$ include concrete examples of the alkynyl group illustrated in $R^1$ and the like in the above general formula (2). Concrete examples of the aryl group in $R^9$ to $R^{16}$ include concrete examples of the aryl group illustrated in $R^1$ and the like in the above general formula (2). Concrete examples of the aromatic heterocyclic group in $R^9$ to $R^{16}$ include concrete examples of the aromatic heterocyclic group illustrated in $R^1$ and the like in the above general formula (2). Concrete examples of the non-aromatic heterocyclic group in $R^9$ to $R^{16}$ include concrete examples of the non-aromatic heterocyclic group illustrated in $R^1$ and the like in the above general formula (2). Concrete examples of the acyl group in $R^9$ to $R^{16}$ include concrete examples of the acyl group illustrated in $R^1$ and the like in the above general formula (2). Concrete examples of the alkoxycarbonyl group in $R^9$ to $R^{16}$ include concrete examples of the alkoxycarbonyl group illustrated in $R^1$ and the like in the above general formula (2). Concrete examples of the aryloxycarbonyl group in $R^9$ to $R^{16}$ include concrete examples of the aryloxycarbonyl group illustrated in $R^1$ and the like in the above general formula (2). Concrete examples of the carbamoyl group in $R^9$ to $R^{16}$ include concrete examples of the carbamoyl group illustrated in $R^1$ and the like in the above general formula (2). Concrete examples of the alkoxy group in $R^9$ to $R^{16}$ include concrete examples of the alkoxy group illustrated in $R^1$ and the like in the above general formula (2). Concrete examples of the aryloxy group in $R^9$ to $R^{16}$ include concrete examples of the aryloxy group illustrated in $R^1$ and the like in the above general formula (2). Concrete examples of the arylthio group in $R^9$ to $R^{16}$ include concrete examples of the arylthio group illustrated in $R^1$ and the like in the above general formula (2). Concrete examples of the alkylamino group in $R^9$ to $R^{16}$ include concrete examples of the alkylamino group illustrated in $R^1$ and the like in the above general formula (2). Concrete examples of the arylamino group in $R^9$ to $R^{16}$ include concrete examples of the arylamino group illustrated in $R^1$ and the like in the above general formula (2). Concrete examples of the silyl group in $R^9$ to $R^{16}$ include concrete examples of the silyl group illustrated in $R^1$ and the like in the above general formula (2). Concrete examples of the siloxy group in $R^9$ to $R^{16}$ include concrete examples of the siloxy group illustrated in $R^1$ and the like in the above general formula (2).

The kind of the substituent on $R^9$ to $R^{16}$ is not particularly limited, and examples include a halogen atom, an alkyl group, an alkenyl group, an alkynyl group, an aryl group, an aromatic heterocyclic group, a non-aromatic heterocyclic group, an acyl group, a carboxyl group, an alkoxycarbonyl group, an aryloxycarbonyl group, a carbamoyl group, a hydroxyl group, an alkoxy group, an aryloxy group, a thiol group, an alkylthio group, an arylthio group, an amino group, an alkylamino group, an arylamino group, a cyano group, a nitro group, a silyl group, a siloxy group and the like. As the substituent on $R^9$ to $R^{16}$, preferably used are a hydrogen atom, an alkyl group, an alkenyl group, an aryl group, a halogen atom and the like.

Concrete examples of the biphenol compound of the general formula (6) include compounds represented by the following formulae (A-1) and (A-2), and an enantiomeric isomer thereof. Particularly preferably used are a compound represented by the following formula (A-1) and an enantiomeric isomer thereof.

[Chemical Formula 16]

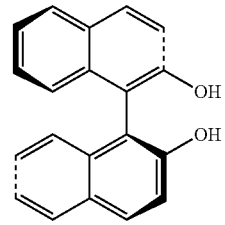

(A-1)

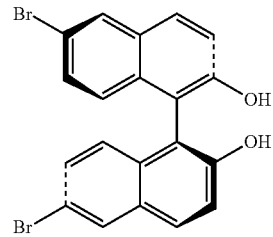

(A-2)

As the above-mentioned optically active biphenol compound, preferably used is also an optically active biphenol compound represented by the following general formula (8),

[Chemical Formula 17]

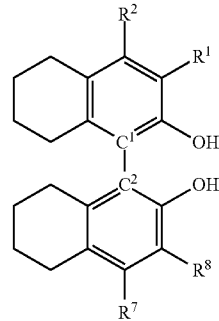

(8)

wherein, in the general formula (8), $R^1$, $R^2$, $R^7$, $R^8$, $C^1$ and $C^2$ are the same as $R^1$, $R^2$, $R^7$, $R^8$, $C^1$ and $C^2$ in the above general formula (5); and each of $C^1$ and $C^2$ has an axial asymmetry in the $C^1$—$C^2$ bond under the aforementioned normal conditions.

Concrete examples of the optically active biphenol compound represented by the general formula (8) include a compound represented by the following formula (A-3) and an enantiomeric isomer thereof,

[Chemical Formula 18]

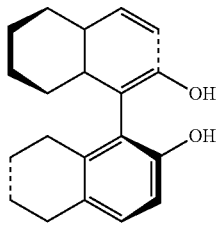

(A-3)

These optically active biphenol compounds are produced in accordance with a known method. For example, the optically active biphenol compound is produced by a known method disclosed in Japanese Laid-open Patent Publication No. 2006-188459, J. Am. Chem. Soc., vol. 129, p. 13927 (2007) or the like.

The optical purity of the above-mentioned optically active biphenol compound is not particularly limited, but it is preferably equal to or more than 80% ee, more preferably equal to or more than 95% ee, and further preferably equal to or more than 97% ee. When the optical purity of the optically active biphenol compound is high, it is excellent because the optical purity of the optically active alcohol to be produced is increased.

The amount of the above-mentioned optically active biphenol compound is not particularly limited so long as it is a catalytic amount (the amount less than equivalents relative to the carbonyl compound), relative to the carbonyl compound used in the present invention. However, it is preferably equal to or more than 0.1 mole % and equal to or less than 50 mole %, based on 100 mole % of the carbonyl compound used in the present invention. The amount of the optically active biphenol compound is more preferably equal to or more than 1 mole % and equal to or less than 20 mole %. When it is in this range, it is excellent because the amount of the optically active biphenol compound is reduced and the optical purity of the optically active alcohol to be produced is increased.

(3) Ether Compound

In the present invention, the reaction is carried out in the presence of an ether compound represented by the following general formula (3),

[Chemical Formula 10]

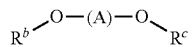

(3)

wherein, in the general formula (3), $R^b$ and $R^c$ are each independently an alkyl group, an alkenyl group or an aryl group, which may have a substituent or may be linked to each other to form a ring.

The structure of the alkyl group in $R^b$ and $R^c$ is not particularly limited, but preferably used is a linear, branched or cyclic alkyl group having equal to or less than 20 carbon atoms. Examples of the linear alkyl group include a methyl group, an ethyl group, an n-propyl group, an n-butyl group, an n-pentyl group, an n-hexyl group, an n-heptyl group, an n-octyl group, an n-nonyl group, an n-decyl group and the like. Examples of the branched alkyl group include an iso-propyl group, an iso-butyl group, a sec-butyl group, a tert-butyl group and the like. Examples of the cyclic alkyl group include a cyclopropyl group, a cyclobutyl group, a cyclopentyl group, a cyclohexyl group, a cycloheptyl group, a cyclooctyl group and the like. The structure of the alkenyl group in $R^b$ and $R^c$ is not particularly limited, but preferably used is a linear, branched or cyclic alkenyl group having equal to or less than 20 carbon atoms. Concrete examples include a vinyl group, an allyl group, a 1-propenyl group and the like. The structure of the aryl group in $R^b$ and $R^c$ is not particularly limited, but preferably used is an aryl group having equal to or less than 22 carbon atoms. Concrete examples include a phenyl group, a naphthyl group, an anthryl group and the like.

The kind of the substituent on $R^b$ and $R^c$ is not particularly limited, and examples include a halogen atom, an alkyl group, an alkenyl group, an alkynyl group, an aryl group, an aromatic heterocyclic group, a non-aromatic heterocyclic group, an acyl group, a carboxyl group, an alkoxycarbonyl group, an aryloxycarbonyl group, a carbamoyl group, a hydroxyl group, an alkoxy group, an aryloxy group, a thiol group, an alkylthio group, an arylthio group, an amino group, an alkylamino group, an arylamino group, a cyano group, a nitro group, a silyl group, a siloxy group and the like.

In the general formula (3), (A) is a group containing one or more carbon atoms, and connects two oxygen atoms in the formula. The structure of (A) is not particularly limited so long as it satisfies the aforementioned conditions. In addition, (A) may contain one or more of an oxygen atom, a nitrogen atom, a sulfur atom, a phosphorus atom, a halogen atom and the like.

Concrete examples of (A) include an alkylene group and an oxyalkylene group. Examples of the aforementioned alkylene group include a methylene group, an ethylene group, a propylene group and the like. Examples of the aforementioned oxyalkylene group include an oxyethylene group, an oxypropylene group and the like. Furthermore, a polymer chain having one of these groups as a monomer unit (for example, a polyoxyethylene chain) is also cited.

As the aforementioned ether compound, it is preferable that each of $R^b$ and $R^c$ is an alkyl group and (A) is an alkylene group, an oxyalkylene group or a polyoxyethylene chain. Concrete examples include dioxane, ethylene glycol dimethyl ether, diethylene glycol dimethyl ether, 12-crown-4,15-crown-5,18-crown-6, polyethylene glycol dimethyl ether and the like. Among these, particularly preferably used is dioxane.

The preferable amount of the aforementioned ether compound depends on the number of ether oxygen atoms contained in the ether compound (an oxygen atom linked to two carbons by a single bond). For example, dioxane contains two ether oxygens. The range of the preferable amount of the ether compound is as follow. In this case, the preferable amount of the ether compound is calculated in terms of the equivalent of ether oxygen relative to 1 equivalent of the aromatic magnesium compound used in the present invention.

The lower limit of the amount of the ether compound is equal to or more than 10 equivalents, preferably equal to or more than 15 equivalents, and more preferably equal to or more than 20 equivalents (for example, dioxane is equal to or more than 5 equivalents, preferably equal to or more than 7.5 equivalents, and more preferably equal to or more than 10 equivalents). When it is in this range, it is excellent because the optical purity of the optically active alcohol to be produced is increased.

On the other hand, the upper limit of the amount of the ether compound is equal to or less than 10,000 equivalents, preferably equal to or less than 1,000 equivalents, and more preferably equal to or less than 400 equivalents (for example, dioxane is equal to or less than 5,000 equivalents, preferably equal to or less than 500 equivalents, and more preferably equal to or less than 200 equivalents). When it is in this range, it is excellent because the rate of the reaction is increased.

(4) Aromatic Magnesium Compound

In the present invention, there is used an aromatic magnesium compound represented by the following general formula (4),

[Chemical Formula 20]

$$R^d_n MgY_{(2-n)} \quad (4)$$

wherein, in the general formula (4), $R^d$ is an aromatic group, which may have a substituent. The aromatic group is not particularly limited so long as it has aromaticity, and concrete examples include an aryl group and an aromatic heterocyclic group. Particularly preferably used is an aryl group. The kind of the substituent on $R^d$ is not particularly limited, and examples include a halogen atom, an alkyl group, an alkenyl group, an alkynyl group, an aryl group, an aromatic heterocyclic group, a non-aromatic heterocyclic group, an acyl group, a carboxyl group, an alkoxycarbonyl group, an aryloxycarbonyl group, a carbamoyl group, a hydroxyl group, an alkoxy group, an aryloxy group, a thiol group, an alkylthio group, an arylthio group, an amino group, an alkylamino group, an arylamino group, a cyano group, a nitro group, a silyl group, a siloxy group and the like.

The structure of the aryl group is not particularly limited, but preferably used is an aryl group having equal to or less than 22 carbon atoms. Concrete examples include a phenyl group, a naphthyl group, an anthryl group and the like.

The structure of the aromatic heterocyclic group is not particularly limited, but preferably used is an aromatic heterocyclic group having equal to or less than 20 carbon atoms. Concrete examples include an imidazolyl group, a furyl group, a thienyl group, a pyridyl group and the like.

In the general formula (4), Y is a halogen atom. The halogen atom is not particularly limited, and examples include a fluorine atom, a chlorine atom, a bromine atom, an iodine atom and the like. Preferable examples of the halogen atom include a chlorine atom, a bromine atom, an iodine atom, and more preferable examples include a chlorine atom and a bromine atom.

The above $R^d$ is a chiral group or an achiral group. The optical purity of the aforementioned magnesium compound is not particularly limited when $R^d$ is a chiral group, but it is preferably equal to or more than 80% ee, more preferably equal to or more than 95% ee, and further preferably equal to or more than 97%. When the optical purity of the aforementioned magnesium compound is high, it is excellent because the diastereo ratio of the optically active alcohol to be produced is increased.

In the general formula (4), n is an integer of 1 or 2.

Examples of the aromatic magnesium compound include phenylmagnesium chloride, phenylmagnesium bromide, 4-methoxyphenylmagnesium chloride, 4-methoxyphenylmagnesium bromide, 4-methylphenylmagnesium chloride, 4-methylphenylmagnesium bromide, 4-chlorophenylmagnesium bromide, diphenylmagnesium, 2-naphthylmagnesium bromide, 2-thienylmagnesium bromide and the like.

The aforementioned aromatic magnesium compound can be produced according to a known method. For example, according to other known methods as disclosed in Organic Synthesis, vol. 80, p. 57 (2003) and the like, an aromatic magnesium compound can be produced. According to other known methods, for example, the reaction is carried out with the addition of a halogenated aromatic compound equivalent to the amount of magnesium to magnesium in an anhydrous solvent. In order to activate magnesium, iodine or the like may be added to the reaction solution. The reaction temperature is not particularly limited, but it is usually in the range of room temperature to the boiling point of the solvent. The reaction time is not particularly limited, but it is usually until the reaction end point determined with the loss of magnesium in the solution. The amount of the solvent is not particularly limited, but the solvent is usually used in an amount such that the concentration of the aromatic magnesium compound in the obtained solution is in the range of 0.1 mol/L to 10 mol/L.

The thus-prepared solution of the aromatic magnesium compound can be used for the present invention after it is purified according to a known method, or without purification. Furthermore, the aforementioned aromatic magnesium compound in a solution state is used for the present invention.

The amount of the aforementioned aromatic magnesium compound is not particularly limited, but it is preferably equal to or more than 100 mole % and equal to or less than 300 mole %, and preferably equal to or more than 100 mole % and equal to or less than 200 mole %, in terms of the equivalent of the aromatic group, based on 100 mole % of the carbonyl compound used in the present invention. In this case, when n in the general formula (4) is 2, the amount of the aromatic magnesium compound is equal to or more than 50 mole % and equal to or less than 150 mole %, and preferably equal to or more than 50 mole % and equal to or less than 100 mole %, in terms of the aromatic magnesium compound, based on 100 mole % of the above carbonyl compound. When it is in this range, it is excellent because the yield of the optically active alcohol is improved, and the amount of the magnesium compound needed to be removed after the reaction is reduced.

(5) Carbonyl Compound

In the present invention, as the carbonyl compound to be a raw material of the optically active alcohol, specifically, aldehyde or ketone may be used, and aldehyde represented by the following general formula (11) is particularly preferably used,

[Chemical Formula 21]

(11)

In the general formula (11), the structure of $R^e$ is not particularly limited, and examples include an alkyl group, an alkenyl group, an alkynyl group, an aryl group, an aromatic heterocyclic group and a non-aromatic heterocyclic group. Particularly preferably used is an aromatic group such as an aryl group, an aromatic heterocyclic group or the like. The kind of the substituent on $R^e$ is not particularly limited, and examples include a halogen atom, an alkyl group, an alkenyl group, an alkynyl group, an aryl group, an aromatic heterocyclic group, a non-aromatic heterocyclic group, an acyl group, a carboxyl group, an alkoxycarbonyl group, an aryloxycarbonyl group, a carbamoyl group, a hydroxyl group, an alkoxy group, an aryloxy group, a thiol group, an alkylthio group, an arylthio group, an amino group, an alkylamino group, an arylamino group, a cyano group, a nitro group, a silyl group, a siloxy group and the like.

The structure of the alkyl group in $R^e$ is not particularly limited, but preferably used is a linear, branched or cyclic alkyl group having equal to or less than 20 carbon atoms. Examples of the linear alkyl group include a methyl group, an ethyl group, an n-propyl group, an n-butyl group, an n-pentyl group, an n-hexyl group, an n-heptyl group, an n-octyl group, an n-nonyl group, an n-decyl group and the like. Examples of the branched alkyl group include an iso-propyl group, an iso-butyl group, a sec-butyl group, a tert-butyl group and the like. Examples of the cyclic alkyl group include a cyclopropyl group, a cyclobutyl group, a cyclopentyl group, a cyclohexyl group, a cycloheptyl group, a cyclooctyl group and the like.

The structure of the alkenyl group in $R^e$ is not particularly limited, but preferably used is a linear, branched or cyclic alkenyl group having equal to or less than 20 carbon atoms. Concrete examples include a vinyl group, an allyl group, a 1-propenyl group and the like.

The structure of the alkynyl group in $R^e$ is not particularly limited, but preferably used is a linear, branched or cyclic alkynyl group having equal to or less than 20 carbon atoms. Concrete examples include an ethynyl group, a propargyl group and the like.

The structure of the aryl group in $R^e$ is not particularly limited, but preferably used is an aryl group having equal to or less than 22 carbon atoms. Concrete examples include a phenyl group, a naphthyl group, an anthryl group and the like.

The structure of the aromatic heterocyclic group in $R^e$ is not particularly limited, but preferably used is an aromatic heterocyclic group having equal to or less than 20 carbon atoms. Concrete examples include an imidazolyl group, a furyl group, a thienyl group, a pyridyl group and the like.

The structure of the non-aromatic heterocyclic group in $R^e$ is not particularly limited, but preferably used is a non-aromatic heterocyclic group having equal to or less than 20 carbon atoms. Concrete examples include a pyrrolidinyl group, a piperidyl group, a tetrahydrofuryl group, a tetrahydropyranyl group and the like.

The above $R^e$ is a chiral group or an achiral group. The optical purity of the aforementioned carbonyl compound is not particularly limited when $R^e$ is a chiral group. When $R^e$ is an achiral group, the optical purity of the aforementioned carbonyl compound is not particularly limited, but it is preferably equal to or more than 80% ee, more preferably equal to or more than 95% ee, and further preferably equal to or more than 97%. When the optical purity of the carbonyl compound is high, it is excellent because the diastereo ratio of the optically active alcohol to be produced is increased.

Examples of the above aldehyde include propionaldehyde, butylaldehyde, valeraldehyde, isovaleraldehyde, hexyldehyde, heptaldehyde, octylaldehyde, nonylaldehyde, decylaldehyde, isobutylaldehyde, 2-methylbutylaldehyde, 2-ethylbutylaldehyde, 2-ethylhexanal, pivalaldehyde, 2,2-dimethylpentanal, cyclopropanecarboaldehyde, cyclohexanecarboaldehyde, phenylacetaldehyde, (4-methoxyphenyl)acetaldehyde, hydroxycinnamaldehyde, benzyloxyacetaldehyde, crotonaldehyde, 3-methylcrotonaldehyde, methacrolein, trans-2-hexenal, cinnamaldehyde, benzaldehyde, o-tolualdehyde, m-tolualdehyde, p-tolualdehyde, 2,4,6-trimethylbenzaldehyde, 4-biphenylcarboaldehyde, 2-fluorobenzaldehyde, 3-fluorobenzaldehyde, 4-fluorobenzaldehyde, 2-chlorobenzaldehyde, 3-chlorobenzaldehyde, 4-chlorobenzaldehyde, 2-bromobenzaldehyde, 3-bromobenzaldehyde, 4-bromobenzaldehyde, 2,3-dichlorobenzaldehyde, 2,4-dichlorobenzaldehyde, 3,4-dichlorobenzaldehyde, 4-(trifluoromethyl)benzaldehyde, 3-hydroxybenzaldehyde, 4-hydroxybenzaldehyde, 3,4-dihydroxybenzaldehyde, o-anisaldehyde, m-anisaldehyde, p-anisaldehyde, 3,4-dimethoxybenzaldehyde, 3,4-(methylenedioxy)benzaldehyde, 2-phenoxybenzaldehyde, 3-phenoxybenzaldehyde, 4-phenoxybenzaldehyde, 2-benzyloxybenzaldehyde, 3-benzyloxybenzaldehyde, 4-benzyloxybenzaldehyde, 1-naphthaldehyde, 2-naphthaldehyde, 2-furancarboaldehyde, 3-furancarboaldehyde, 2-thiophenecarboaldehyde, 3-thiophenecarboaldehyde, 1-benzothiophene-3-carboaldehyde, N-methylpyrrole-2-carboaldehyde, 1-methylindole-3-carboaldehyde, 2-pyridinecarboaldehyde, 3-pyridinecarboaldehyde, 4-pyridinecarboaldehyde, 4-tert-butylbenzaldehyde, 4-methoxybenzaldehyde, 4-trifluoromethylbenzaldehyde, 2-octynal and the like.

(6) Optically Active Alcohol

The optically active alcohol in the present invention is obtained by reacting the aforementioned titanium compound, the aforementioned aromatic magnesium compound and the aforementioned carbonyl compound in the presence of a catalytic amount of the aforementioned optically active biphenol compound and the aforementioned ether compound.

Furthermore, in order to produce the aforementioned optically active alcohol, a reaction resulting from mixing the aforementioned five compounds (the titanium compound, the optically active biphenol compound, the ether compound, the aromatic magnesium compound, and the carbonyl compound) and other substances according to the reaction procedure to be described below will be described hereinafter as the reaction of the present invention.

The reaction of the present invention includes a reaction in which the aromatic group in the aforementioned aromatic magnesium compound is 1,2-added to the carbonyl group in the aforementioned carbonyl compound, so that a novel carbon-carbon bond is enantioselectively formed, and at the same time a carbon-oxygen double bond of the carbonyl group becomes a carbon-oxygen single bond.

In the present invention, for example, when the aforementioned aldehyde represented by the general formula (11) is used as the aforementioned carbonyl compound and the aromatic magnesium compound represented by the general formula (4) is used as the aforementioned aromatic magnesium compound, an optically active alcohol represented by the following general formula (12) is obtained,

[Chemical Formula 22]

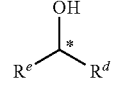

(12)

wherein, in the general formula (12), $R^d$ represents the same groups as $R^d$ in the general formula (4); $R^e$ represents the same group as $R^e$ in the general formula (11); and the mark * represents an asymmetric carbon atom.

Examples of the aforementioned optically active alcohol according to the present invention include optically active compounds such as propylphenylmethanol, butylphenylmethanol, t-butylphenylmethanol, iso-butylphenylmethanol, hexylphenylmethanol, heptylphenylmethanol, octylphenylmethanol, nonylphenylmethanol, decylphenylmethanol, 2-methylbutylphenylmethanol, 2-ethylbutylphenylmethanol, 2,2-dimethylpentylphenylmethanol, cyclopropylphenylmethanol, cyclohexylphenylmethanol, 2-methylbenzhydrol, 3-methylbenzhydrol, 4-methylbenzhydrol, 2-methoxybenzhydrol, 3-methoxybenzhydrol, 4-methoxybenzhydrol, 2-chlorobenzhydrol, 3-chlorobenzhydrol, 4-chlorobenzhydrol, 2-bromobenzhydrol, 3-bromobenzhydrol, 4-bromobenzhydrol, 2-fluorobenzhydrol, 3-fluorobenzhydrol, 4-fluorobenzhydrol, 2,3-dichlorobenzhydrol, 2,4-dichlorobenzhydrol, 3,4-dichlorobenzhydrol, 4-(trifluoromethyl)benzhydrol, 3-hydroxybenzhydrol, 4-hydroxybenzhydrol, 3,4-dihydroxybenzhydrol, 3,4-dimethoxybenzhydrol, 3,4-(methylenedioxy)benzhydrol, 2-phenoxybenzhydrol, 3-phenoxybenzhydrol, 4-phenoxybenzhydrol, 2-benzyloxybenzhydrol, 3-benzyloxybenzhydrol, 4-benzyloxybenzhydrol, 1-naphthylphenylmethanol, 2-naphthylphenylmethanol, 2-furylphenylmethanol, 3-furylphenylmethanol, 2-thienylphenylmethanol, 3-thienylphenylmethanol, 1-benzothienylphenylmethanol, N-methylpyrrole-2-phenylmethanol, 1-methylindole-3-phenylmethanol, 2-pyridylphenylmethanol, 3-pyridylphenylmethanol, 4-pyridylphenylmethanol, 4-tert-butylbenzhydrol, 4-trifluoromethylbenzhydrol, 1-phenylocta-2-in-1-ol, trans-1,3-diphenyl-propa-2-en-1-ol and the like.

The aforementioned optically active alcohol according to the present invention is useful as a synthetic raw material for synthetic intermediates of drugs and agricultural chemicals, functional materials, or other fine chemicals.

(7) Reaction Procedure

Hereinafter, the procedure involved in carrying out the present invention will be described.

In the reaction of the present invention, the order of mixing the above compounds is not particularly limited. Furthermore, the amount of the above compounds used for the reaction may be added at one time, or may be added two or more times.

Preferable examples of the reaction procedure include the following.

(1) It is preferable that the aforementioned titanium compound and the aforementioned aromatic magnesium compound are mixed in the presence or absence of the aforementioned optically active biphenol compound, in the presence or absence of the aforementioned ether compound, and in the absence of the aforementioned carbonyl compound. The time until the carbonyl compound is added after mixing of the aforementioned titanium compound with the aforementioned aromatic magnesium compound is not particularly limited, but it is preferably from 1 minute to 2 hours and more preferably from 5 minutes to 30 minutes.

(2) It is preferable that the aforementioned titanium compound and the aforementioned optically active biphenol compound are mixed in the presence or absence of the aforementioned ether compound, in the presence or absence of the aforementioned aromatic magnesium compound, and in the absence of the aforementioned carbonyl compound. When the aforementioned titanium compound and the optically active biphenol compound are mixed, it is considered that a complex forming reaction occurs to form a titanium-biphenol complex. The time until the aforementioned carbonyl compound is added after mixing of the aforementioned titanium compound with the optically active biphenol compound is not particularly limited, but it is preferably from 5 minutes to 2 hours and more preferably from 30 minutes to 1 hour.

(3) It is preferable that the aforementioned ether compound and the aforementioned aromatic magnesium compound are mixed in the presence or absence of the aforementioned titanium compound, in the presence or absence of the aforementioned optically active biphenol compound, and in the absence of the aforementioned carbonyl compound. After mixing, the aforementioned carbonyl compound is added after a predetermined period of time.

More Preferable examples of the reaction procedure include the following.

(1) The aforementioned aromatic magnesium compound and the aforementioned ether compound are mixed in the absence of the aforementioned titanium compound, the aforementioned optically active biphenol compound and the aforementioned carbonyl compound, and then the aforementioned titanium compound, the aforementioned optically active biphenol compound and the aforementioned carbonyl compound are added to the mixture in order. In this case, it is preferable that, after addition of the above optically active biphenol compound, the mixture is placed preferably for 5 minutes to 2 hours and more preferably for 30 minutes to 1 hour, and then the aforementioned carbonyl compound is added.

(2) The aforementioned titanium compound and the aforementioned aromatic magnesium compound are mixed in the absence of the aforementioned ether compound, the aforementioned optically active biphenol compound and the aforementioned carbonyl compound, and then the aforementioned ether compound, the aforementioned optically active biphenol compound and the aforementioned carbonyl compound are added to the mixture in order. In this case, it is preferable that, after addition of the aforementioned optically active biphenol compound, the mixture is placed preferably for 5 minutes to 2 hours and more preferably for 30 minutes to 1 hour, and then the aforementioned carbonyl compound is added.

(3) A mixture obtained by adding the aforementioned ether compound, the aforementioned titanium compound and the aforementioned optically active biphenol compound dropwise to the aforementioned aromatic magnesium compound in order is added to the aforementioned carbonyl compound in the absence of the aforementioned titanium compound, the aforementioned optically active biphenol compound and the aforementioned carbonyl compound. In this case, it is preferable that the mixture after addition of the aforementioned optically active biphenol compound is placed preferably for 5 minutes to 2 hours and more preferably for 30 minutes to 1 hour, and then added to the aforementioned carbonyl compound over a period of 1 minute to 2 hours and more preferably over a period of 3 minutes to 30 minutes.

Herein, the estimated method for producing alcohol of the present invention will be described.

First, in the reaction of the present invention, the aromatic group in the aforementioned aromatic magnesium compound is moved on the aforementioned titanium compound, and then reacted with the carbonyl compound. In this case, a magnesium salt is generated. Even when the aforementioned aromatic magnesium compound and the ether compound are mixed, the same magnesium salt is generated in some cases. These magnesium salts cause a reduction of enantioselectivity in the reaction of the present invention. The aforementioned ether compound, particularly dioxane, forms a complex with the magnesium salt so that its solubility is lowered. Furthermore, it is considered that the adverse effects of the magnesium salt are eliminated without removing the magnesium salt by adjusting the amount of the ether compound to be added, the structure of a catalyst and the kind of a solvent, and as a result, the enantioselectivity is enhanced. From the above reason, in the process of producing an alcohol of the present invention, the magnesium salt is not necessarily removed from the reaction system, and high enantioselectivity is considered to be maintained even in the presence of the magnesium salt.

As described above, in the process of producing an optically active alcohol of the present invention, a particle component such as a magnesium salt or the like is generated to become a suspension in some cases. A transparent solution obtained by separating the particle component from the suspension by a known method such as filtration, centrifugal separation or the like is used for the reaction of the present invention. The solution may be used for the present invention as it is without subjecting the suspension to a special separation operation. It is preferable that, in all steps of the production method of the present invention, the particle component may not be separated. Thus, according to the present invention, the method for producing an optically active alcohol suitable for upscaling is achieved.

In the reaction of the present invention, it is preferable to use a solvent. Since the aromatic magnesium compound in a solution state is usually used for the present invention, a solvent of the aromatic magnesium compound solution may be used as a solvent of the present invention as it is. When the aforementioned diether compound is a liquid, the diether compound may be used as a solvent. Furthermore, an additional solvent may be added during the reaction of the present invention. The stage of the reaction for the addition of a solvent is not particularly limited.

The solvent in use is not particularly limited, and preferable examples include halogenated hydrocarbon solvents such as dichloromethane, chloroform, 1,2-dichloroethane, chlorobenzene and the like; aromatic hydrocarbon solvents such as toluene, xylene and the like; and ether solvents such as tetrahydrofuran, dioxane, diethyl ether, dimethoxyethane, cyclopentyl methyl ether and the like. Among these, particularly preferably used are halogenated solvents and ether solvents. Furthermore, these may be used singly or as a mixed solvent. The total amount of the solvent is preferably equal to or more than about 0.5 mL and equal to or less than about 50 mL, and more preferably equal to or more than about 2 mL and equal to or less than about 20 mL, based on 1 millimole of the carbonyl compound as a substrate.

In the reaction of the present invention, usually, after addition of the aforementioned five compounds (the titanium compound, the optically active biphenol compound, the ether compound, the aromatic magnesium compound and the carbonyl compound) for the reaction for a predetermined period of time, a substance containing an active proton is added to terminate the reaction. Examples of the substance containing an active proton include proton acid such as hydrochloric acid, sulfuric acid, nitric acid or the like, water, alcohol and the like. Preferably used is proton acid. Preferable concrete examples of the substance containing an active proton include 1N hydrochloric acids.

The reaction of the present invention may be carried out without stirring or with stirring. The reaction is preferably carried out with stirring from the fact that the reaction is carried out reproducibly and uniformly. A method of stirring the reaction solution is not particularly limited, and a known method may be used.

In the reaction of the present invention, the reaction temperature is not particularly limited, but it is preferably equal to or more than −80 degrees centigrade and equal to or less than 100 degrees centigrade, more preferably equal to or more than −30 degrees centigrade and equal to or less than 50 degrees centigrade, and further preferably equal to or more than 0 degree centigrade and equal to or less than 30 degrees centigrade. When it is in this range, it is excellent because both shortening of the reaction time and improvement of the optical purity of the optically active alcohol to be obtained are combined.

In the reaction of the present invention, the reaction time of the aforementioned aromatic magnesium compound and the aforementioned carbonyl compound is not particularly limited, but it is usually equal to or more than 10 minutes and equal to or less than 24 hours, and preferably equal to or more than 30 minutes and equal to or less than 5 hours. When it is in this range, it is excellent because both shortening of the reaction time and improvement of the reaction yield are combined.

The optically active alcohol obtained by the present invention may also be purified and isolated according to a known method. Examples of the purification method include recrystallization, distillation, column chromatography and the like.

The optically active alcohol obtained by the present invention may be derivatized using a known method. In this case, the optically active alcohol isolated after carrying out the above purification may be derivatized, or a liquid mixture containing an unpurified optically active alcohol may be subjected to the appropriate operation and derivatized.

After the reaction of the present invention, the aforementioned optically active biphenol compound may be separated and reused by a known method. Examples of the separation method include recrystallization, column chromatography and the like.

Hereinafter, the present invention is illustrated in detail by way of Examples, but the present invention is not limited to these Examples.

The identification of the optically active alcohol according to the present invention was carried out by comparing $^1$H NMR spectrum (using Bruker400, commercially available from Bruker Co., Ltd.) in a deuterated chloroform solvent to previously reported values. The conversion rate of asymmetric arylation and the enantiomeric excess were measured by the use of high-performance liquid chromatography (Model 2695, commercially available from Waters Co. Ltd.) or gas chromatography (Model 6890N, commercially available from Agilent Technologies Inc.). In this case, as an optically active column, there was used CHIRALPAK OD-H, AD-H, OJ-H, OB—H (commercially available from Daicel Chemical Industries, Ltd.) or CHIRALDEX G-TA (commercially available from Advanced Separation Technologies Inc.). The absolute configuration of an optically active benzhydrol was determined by comparing the retention time of high-performance liquid chromatography or gas chromatography to previously reported values.

In Examples, as the solvent, a commercial anhydrous solvent was used. Dichloromethane (hereinafter referred to as the anhydrous dichloromethane) in use was a product of Kanto Chemical Co., Inc. Reagents commercially available from Sigma-Aldrich Pte Ltd. were used without purification for a THF solution (1.0 mol/L) of 1,4-dioxane (hereinafter referred to as the anhydrous 1,4-dioxane), tetrahydrofuran (THF) (hereinafter referred to as the anhydrous THF), tetra-iso-propoxy titanium, titanium tetrachloride and phenylmagnesium bromide; magnesium, bromobenzene, 4-tolualdehyde, (R)-1,1'-binaphthalene-2,2'-diol (hereinafter referred to as the (R)-BINOL), (R)-5,5',6,6',7,7',8,8'-octahydro(1,1'-binaphthalene)-2,2'-diol (hereinafter referred to as the (R)—H8-BINOL), (4R,5R)-2,2'-α,α,α',α'-tetraphenyldioxalene-4,5-dimethanol (hereinafter referred to as the (−)-TADOL), and the aforementioned compounds. With respect to other compounds, commercial reagents were used without purification.

All reactions were carried out in a nitrogen atmosphere. As an appliance used for the reaction, a sufficiently dried appliance was used.

EXAMPLES

First, Preparation Examples will be described below.

Preparation Example 1

0.38 g (2.0 mmol) of titanium tetrachloride and 2 mL of anhydrous dichloromethane were weighed in a test tube equipped with a lid, and 1.7 g (6.0 mmol) of tetra-iso-propoxy titanium was added dropwise thereto while stirring. After stirring at room temperature for 60 minutes, the reaction solution was transferred to a 10-mL volumetric flask, and anhydrous dichloromethane was added thereto for diluting to 10 mL, whereby a uniform, colorless and transparent dichloromethane solution (0.80 mol/L) of chloro-tri-iso-propoxy titanium was obtained.

Preparation Example 2

0.73 g (30 mmol) of magnesium and 20 mL of anhydrous dioxane were weighed in a round-bottom flask, and a small amount of iodine was put thereinto, and the system was stirred at 100 degrees centigrade for 30 minutes to activate magnesium. After the reaction solution was cooled to room temperature, 4.7 g (30 mmol) of bromobenzene was added thereto and refluxed at 110 degrees centigrade for 16 hours. The obtained dioxane solution containing a white precipitate was transferred to a container for a centrifugal separator in a nitrogen atmosphere and centrifuged at 4,600 rpm for 30 minutes, and the obtained yellow transparent supernatant liquid was transferred to a sample bottle. The obtained anhydrous 1,4-dioxane solution of diphenylmagnesium was titrated using 1,10-phenanthroline, and its concentration was found to be 1.1 mol/L.

Preparation Example 3

0.24 g (10 mmol) of magnesium and 10 mL of anhydrous THF were weighed in a round-bottom flask, and a small amount of iodine was put thereinto, and the system was stirred at room temperature for minutes to activate magnesium. 1.8 g (10 mmol) of 4-chlorobenzene bromide was added at room temperature thereto, and the contents were stirred at room temperature for 2 hours. The obtained anhydrous THF solution of 4-chlorophenylmagnesium bromide was titrated using 1,10-phenanthroline, and its concentration was found to be 0.80 mol/L.

Preparation Example 4

0.24 g (10 mmol) of magnesium and 10 mL of anhydrous THF were weighed in a round-bottom flask, and a small amount of iodine was put thereinto, and the system was stirred at room temperature for minutes to activate magnesium. 1.8 g (10 mmol) of 4-methoxybenzene bromide was added at room temperature thereto, and the contents were stirred at room temperature for 2 hours. The obtained anhydrous THF solution of 4-methoxyphenylmagnesium bromide was titrated using 1,10-phenanthroline, and its concentration was found to be 0.80 mol/L.

Subsequently, Examples will be illustrated below.

Example 1

0.50 mL (0.40 mmol) of an anhydrous dichloromethane solution (0.80 mol/L) of chloro-tri-iso-propoxy titanium prepared in Preparation Example 1 was added to 0.47 mL (0.38 mmol) of an anhydrous 1,4-dioxane solution (0.81 mol/L) of diphenylmagnesium prepared in Preparation Example 2, and the contents were stirred for 10 minutes, and then 0.50 mL (0.025 mmol) of an anhydrous dichloromethane solution (0.050 mol/L) of (R)—H8-BINOL was added thereto, and stirred at room temperature for 30 minutes. 30 mg (0.250 mmol) of p-tolualdehyde was added to the thus-obtained solution containing a white precipitate, and the contents were stirred at room temperature for 1 hour for the reaction. Thereafter, 2.0 mL of 1N hydrochloric acid was added and stirred for 10 minutes, and then the solution was extracted with hexane. The obtained organic layer was purified with silica gel column to obtain 4-methylbenzhydrol in which the (R) form was in excess. The conversion rate of the raw material was 95%, while the enantiomeric excess of the product was 94% ee. The amount of dioxane used during the reaction was 11 equivalents (22 equivalents in terms of the ether oxygen equivalent) relative to magnesium.

Example 2

0.50 mL (0.0250 mmol) of an anhydrous dichloromethane solution (0.050 mol/L) of (R)—H8-BINOL was added to 0.50 mL (0.40 mmol) of an anhydrous dichloromethane solution (0.80 mol/L) of chloro-tri-iso-propoxy titanium prepared in Preparation Example 1, and the contents were stirred for 10 minutes, and then 0.36 mL (0.40 mmol) of an anhydrous 1,4-dioxane solution (1.1 mol/L) of diphenylmagnesium prepared in Preparation Example 2 was added thereto, and stirred at room temperature for 30 minutes. Thereafter, an operation was carried out in the same manner as in Example 1 to obtain 4-methylbenzhydrol in which the (R) form was in excess. The conversion rate of the raw material was 95%, while the enantiomeric excess of the product was 92% ee.

Example 3

An operation was carried out in the same manner as in Example 1, except that 1.0 mL (12 mmol) of anhydrous 1,4-dioxane was mixed to 0.40 mL (0.40 mmol) of an anhydrous THF solution (1.0 mol/L) of commercial phenylmagnesium bromide instead of the anhydrous 1,4-dioxane solution of diphenylmagnesium, and the obtained solution containing a white precipitate was used. Thus, 4-methylbenzhydrol in which the (R) form was in excess was obtained. The conversion rate of the raw material was 96%, while the enantiomeric excess was 92% ee. The amount of dioxane used during the reaction was 30 equivalents (60 equivalents in terms of the ether oxygen equivalent) relative to magnesium.

Example 4

An operation was carried out in the same manner as in Example 1, except that 0.50 mL (0.0250 mmol) of an anhydrous dichloromethane solution (0.050 mol/L) of (R)-BINOL was used instead of the anhydrous dichloromethane solution of (R)—H8-BINOL in Example 1. Thus, 4-methylbenzhydrol in which the (R) form was in excess was obtained. The conversion rate of the raw material was 95%, while the enantiomeric excess was 85% ee.

Example 5

An operation was carried out in the same manner as in Example 1, except that 0.50 mL (0.013 mmol) of an anhydrous dichloromethane solution (0.0250 mol/L) of (R)—H8-BINOL was used instead of the anhydrous dichloromethane solution of (R)—H8-BINOL in Example 1. Thus, 4-methylbenzhydrol in which the (R) form was in excess was obtained. The conversion rate of the raw material was 95%, while the enantiomeric excess was 85% ee.

Example 6

An operation was carried out in the same manner as in Example 1, except that 0.50 mL (0.40 mmol) of an anhydrous dichloromethane solution (0.80 mol/L) of dichloro-di-iso-propoxy titanium was used instead of the anhydrous dichloromethane solution of chloro-tri-iso-propoxy titanium. Thus, 4-methylbenzhydrol in which the (R) form was in excess was obtained. The conversion rate of the raw material was 96%, while the enantiomeric excess was 92% ee.

Example 7

An operation was carried out in the same manner as in Example 1, except that 35 mg (0.25 mmol) of 4-chlorobenzaldehyde was used instead of p-tolualdehyde. Thus, 4-chlorobenzhydrol in which the (R) form was in excess was obtained. The conversion rate of the raw material was 92%, while the enantiomeric excess was 90% ee.

Example 8

An operation was carried out in the same manner as in Example 1, except that 34 mg (0.25 mmol) of p-anisaldehyde was used instead of p-tolualdehyde. Thus, 4-methoxybenzhydrol in which the (R) form was in excess was obtained. The conversion rate of the raw material was 90%, while the enantiomeric excess was 88% ee.

Example 9

An operation was carried out in the same manner as in Example 1, except that 39 mg (0.25 mmol) of 1-naphthaldehyde was used instead of p-tolualdehyde. Thus, naphthylphenylmethanol in which the (R) form was in excess was obtained. The conversion rate of the raw material was 89%, while the enantiomeric excess was 96% ee.

Example 10

An operation was carried out in the same manner as in Example 1, except that 28 mg (0.25 mmol) of cyclohexanecarboxaldehyde was used instead of p-tolualdehyde. Thus, cyclohexylphenylmethanol in which the (S) isomer was in excess was obtained. The conversion rate of the raw material was 94%, while the enantiomeric excess was 94% ee.

Example 11

An operation was carried out in the same manner as in Example 1, except that 34 mg (0.25 mmol) of hydroxycinnamaldehyde was used instead of p-tolualdehyde. Thus, 1,3-diphenyl-1-propanol in which the (S) isomer was in excess was obtained. The conversion rate of the raw material was 90%, while the enantiomeric excess was 87% ee.

Example 12

An operation was carried out in the same manner as in Example 2, except that 0.50 mL (0.40 mmol) of an anhydrous THF solution (0.80 mol/L) of 4-chlorophenylmagnesium bromide prepared in Preparation Example 3 was used instead of the anhydrous THF solution of phenylmagnesium bromide, and 27 mg (0.25 mmol) of benzaldehyde was used instead of p-tolualdehyde. Thus, 4-chlorobenzhydrol in which the (S) isomer was in excess was obtained. The conversion rate of the raw material was 96%, while the enantiomeric excess was 91% ee. The amount of dioxane used during the reaction was 30 equivalents (60 equivalents in terms of the ether oxygen equivalent) relative to magnesium.

Example 13

An operation was carried out in the same manner as in Example 2, except that 0.50 mL (0.40 mmol) of an anhydrous THF solution (0.80 mol/L) of 4-methoxyphenylmagnesium bromide prepared in Preparation Example 4 was used instead of the anhydrous THF solution of phenylmagnesium bromide, and 27 mg (0.25 mmol) of benzaldehyde was used instead of p-tolualdehyde. Thus, 4-methoxybenzhydrol in which the (S) isomer was in excess was obtained. The conversion rate of the raw material was 92%, while the enantiomeric excess was 93% ee. The amount of dioxane used during the reaction was 30 equivalents (60 equivalents in terms of the ether oxygen equivalent) relative to magnesium.

Example 14

1.0 mL (12 mmol) of anhydrous 1,4-dioxane was added to 0.375 mL (0.375 mmol) of an anhydrous THF solution (1.00 mol/L) of commercial phenylmagnesium bromide, and the contents were stirred for 10 minutes, and then 0.402 mL (0.325 mmol) of an anhydrous dichloromethane solution (0.80 mol/L) of chloro-tri-iso-propoxy titanium prepared in Preparation Example 1 was added thereto, and further stirred for 10 minutes. 0.25 mL (0.0125 mmol) of an anhydrous dichloromethane solution (0.050 mol/L) of (R)—H8-BINOL was added thereto and stirred at room temperature for 30 minutes. The thus-obtained solution containing a white precipitate was added dropwise to 30 mg (0.25 mmol) of a dichloromethane solution (0.5 mL) of p-tolualdehyde using a syringe over a period of 10 minutes, and stirred at room temperature for 1 hour for the reaction. Thereafter, an operation was carried out in the same manner as in Example 1 to obtain (R)-4-methylbenzhydrol. The conversion rate of the raw material was 80%, while the enantiomeric excess of the product was 94% ee. The amount of dioxane used during the reaction was 32 equivalents (64 equivalents in terms of the ether oxygen equivalent) relative to magnesium.

Example 15

An operation was carried out in the same manner as in Example 14, except that 41 mg (0.25 mmol) of 4-tert-butylbenzaldehyde was used instead of p-tolualdehyde. Thus, (R)-4-tert-butylbenzhydrol was obtained. The conversion rate of the raw material was 98%, while the enantiomeric excess was 90% ee.

Example 16

An operation was carried out in the same manner as in Example 14, except that 35 mg (0.25 mmol) of 4-chlorobenzaldehyde was used instead of p-tolualdehyde. Thus, (R)-4-chlorobenzhydrol was obtained. The conversion rate of the raw material was 61%, while the enantiomeric excess was 93% ee.

Example 17

An operation was carried out in the same manner as in Example 14, except that 35 mg (0.25 mmol) of 3-chlorobenzaldehyde was used instead of p-tolualdehyde. Thus, (R)-3-chlorobenzhydrol was obtained. The conversion rate of the raw material was 77%, while the enantiomeric excess was 89% ee.

Example 18

An operation was carried out in the same manner as in Example 14, except that 35 mg (0.25 mmol) of 2-chlorobenzaldehyde used instead of p-tolualdehyde. Thus, (R)-2-chlorobenzhydrol was obtained. The conversion rate of the raw material was 96%, while the enantiomeric excess was 92% ee.

Example 19

An operation was carried out in the same manner as in Example 14, except that 34 mg (0.25 mmol) of 4-methoxybenzaldehyde was used instead of p-tolualdehyde. Thus, (R)-4-methoxybenzhydrol was obtained. The conversion rate of the raw material was 91%, while the enantiomeric excess was 92% ee.

Example 20

An operation was carried out in the same manner as in Example 14, except that 44 mg (0.25 mmol) of 4-trifluoromethylbenzaldehyde was used instead of p-tolualdehyde. Thus, (R)-4-trifluoromethylbenzhydrol was obtained. The conversion rate of the raw material was 87%, while the enantiomeric excess was 92% ee.

Example 21

An operation was carried out in the same manner as in Example 14, except that 39 mg (0.25 mmol) of 1-naphthaldehyde was used instead of p-tolualdehyde. Thus, (R)-1-naphthylphenylmethanol was obtained. The conversion rate of the raw material was 95%, while the enantiomeric excess was 92% ee.

Example 22

An operation was carried out in the same manner as in Example 14, except that 39 mg (0.25 mmol) of 2-naphthaldehyde was used instead of p-tolualdehyde. Thus, (R)-2-naphthylphenylmethanol was obtained. The conversion rate of the raw material was 95%, while the enantiomeric excess was 84% ee.

Example 23

An operation was carried out in the same manner as in Example 14, except that 33 mg (0.25 mmol) of cinnamaldehyde was used instead of p-tolualdehyde. Thus, (R)-trans-1, 3-diphenyl-propa-2-en-1-ol was obtained. The conversion rate of the raw material was 96%, while the enantiomeric excess was 86% ee.

Example 24

An operation was carried out in the same manner as in Example 14, except that 32 mg (0.25 mmol) of 2-octynal was used instead of p-tolualdehyde. Thus, (R)-1-phenylocta-2-in-1-ol was obtained. The conversion rate of the raw material was 95%, while the enantiomeric excess was 88% ee.

Example 25

An operation was carried out in the same manner as in Example 14, except that 27 mg (0.25 mmol) of 3-pyridinecarboaldehyde was used instead of p-tolualdehyde. Thus, (R)-3-pyridylphenylmethanol was obtained. The conversion rate of the raw material was 91%, while the enantiomeric excess was 83% ee.

Example 26

An operation was carried out in the same manner as in Example 14, except that 24 mg (0.25 mmol) of 2-furancarboaldehyde was used instead of p-tolualdehyde. Thus, (R)-2-furylphenylmethanol was obtained. The conversion rate of the raw material was 65%, while the enantiomeric excess was 73% ee.

Example 27

An operation was carried out in the same manner as in Example 14, except that 29 mg (0.25 mmol) of heptaldehyde was used instead of p-tolualdehyde. Thus, (R)-heptylphenylmethanol was obtained. The conversion rate of the raw material was 85%, while the enantiomeric excess was 90% ee.

Example 28

An operation was carried out in the same manner as in Example 14, except that 28 mg (0.25 mmol) of cyclohexanecarboaldehyde was used instead of p-tolualdehyde. Thus, (R)-cyclohexylphenylmethanol was obtained. The conversion rate of the raw material was 83%, while the enantiomeric excess was 92% ee.

Example 29

An operation was carried out in the same manner as in Example 14, except that 22 mg (0.25 mmol) of valeraldehyde was used instead of p-tolualdehyde. Thus, (R)-t-butylphenylmethanol was obtained. The conversion rate of the raw material was 75%, while the enantiomeric excess was 86% ee.

Example 30

An operation was carried out in the same manner as in Example 14, except that 0.29 mL (0.375 mmol) of 4-chlorophenylmagnesium bromide (1.4 mol/L) prepared from magnesium and 4-chlorobenzene bromide was used instead of the anhydrous THF solution of phenylmagnesium bromide. Thus, (S)-4-chlorobenzhydrol was obtained. The conversion rate of the raw material was 96%, while the enantiomeric excess was 92% ee.

Example 31

An operation was carried out in the same manner as in Example 14, except that 0.22 mL (0.375 mmol) of 4-methoxyphenylmagnesium bromide (1.7 mol/L) prepared from magnesium and 4-methoxybenzene bromide was used instead of the anhydrous THF solution of phenylmagnesium bromide. Thus, (S)-4-methoxybenzhydrol was obtained. The conversion rate of the raw material was 98%, while the enantiomeric excess was 92% ee.

Example 32

An operation was carried out in the same manner as in Example 14, except that 0.63 mL (0.375 mmol) of 2-naphthylmagnesium bromide (0.60 mol/L) prepared from magnesium and 2-bromonaphthalene was used instead of the anhydrous THF solution of phenylmagnesium bromide. Thus, (S)-

1-naphthylphenylmethanol was obtained. The conversion rate of the raw material was 99%, while the enantiomeric excess was 80% ee.

Example 33

An operation was carried out in the same manner as in Example 14, except that 0.375 mL (0.375 mmol) of commercial 2-thienylmagnesium bromide (1.0 mol/L) was used instead of the anhydrous THF solution of phenylmagnesium bromide. Thus, (S)-2-thienylphenylmethanol was obtained. The conversion rate of the raw material was 89%, while the enantiomeric excess was 69% ee.

Furthermore, Comparative Examples will be described below.

Comparative Example 1

An operation was carried out in the same manner as in Example 1, except that 0.40 mL (0.40 mmol) of an anhydrous THF solution (1.0 mol/L) of phenylmagnesium bromide was used instead of the anhydrous 1,4-dioxane solution of diphenylmagnesium. Thus, (R)-4-methylbenzhydrol was obtained. The conversion rate of the raw material was 98%, while the enantiomeric excess was 39% ee.

Comparative Example 2

An operation was carried out in the same manner as in Example 1, except that 0.50 mL (0.025 mmol) of an anhydrous dichloromethane solution (0.050 mol/L) of (−)-TADOL was used instead of the anhydrous dichloromethane solution of (R)—H8-BINOL. Thus, (S)-4-methylbenzhydrol was obtained. The conversion rate of the raw material was 95%, while the enantiomeric excess was 17% ee.

The present application claims priority based on Japanese patent application No. 2009-79953 filed on Mar. 27, 2009, and incorporates herein the entire disclosure thereof by reference.

The invention claimed is:

1. A method for producing an optically active alcohol comprising reacting a titanium compound represented by the following general formula (1), an aromatic magnesium compound represented by the following general formula (4) and a carbonyl compound in the presence of an optically active biphenol compound represented by the following general formula (2) and an ether compound represented by the following general formula (3), $$Ti(OR^a)_m X_{(4-m)} \quad (1)$$

wherein, in the formula, $R^a$ is an alkyl group, an alkenyl group, an aryl group or an acyl group, which may have a substituent; X is a halogen atom; and m is an integer of 0 to 4,

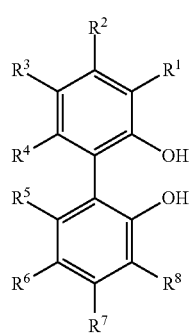

(2)

wherein, in the formula, $R^1$ to $R^8$ are each independently a hydrogen atom, a halogen atom, an alkyl group, an alkenyl group, an alkynyl group, an aryl group, an aromatic heterocyclic group, a non-aromatic heterocyclic group, an acyl group, a carboxyl group, an alkoxycarbonyl group, an aryloxycarbonyl group, a carbamoyl group, a hydroxyl group, an alkoxy group, an aryloxy group, a thiol group, an alkylthio group, an arylthio group, an amino group, an alkylamino group, an arylamino group, a cyano group, a nitro group, a silyl group or a siloxy group, which may have a substituent or may be linked to each other to form a ring,

(3)

wherein, in the formula, $R^b$ and $R^c$ are each independently an alkyl group, an alkenyl group or an aryl group, which may have a substituent or may be linked to each other to form a ring; and (A) is a group containing one or more carbon atoms, which connects two oxygen atoms in the formula, $$R^d_n MgY_{(2-n)} \quad (4)$$

wherein, in the formula, $R^d$ is an aromatic group, which may have a substituent; Y is a halogen atom; and n is an integer of 1 or 2.

2. The method for producing an optically active alcohol according to claim 1, in which said optically active biphenol compound is represented by the following general formula (5),

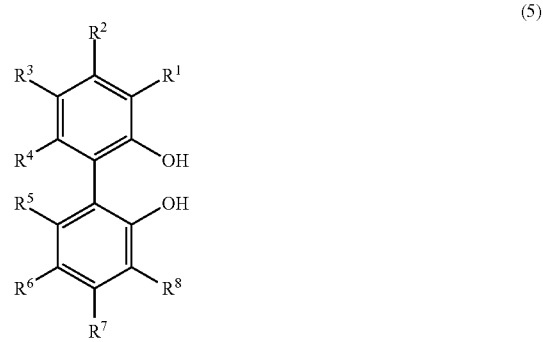

(5)

wherein, in the formula, $R^1$ to $R^8$ are each independently a hydrogen atom, a halogen atom, an alkyl group, an alkenyl group, an alkynyl group, an aryl group, an aromatic heterocyclic group, a non-aromatic heterocyclic group, an acyl group, a carboxyl group, an alkoxycarbonyl group, an aryloxycarbonyl group, a carbamoyl group, a hydroxyl group, an alkoxy group, an aryloxy group, a thiol group, an alkylthio group, an arylthio group, an amino group, an alkylamino group, an arylamino group, a cyano group, a nitro group, a silyl group or a siloxy group, which may have a substituent or may be linked to each other to form a ring; and at least one of $R^4$ and, $R^5$ is not a hydrogen atom.

3. The method for producing an optically active alcohol according to claim 1, in which said optically active biphenol compound is represented by the following general formula (6), (6)

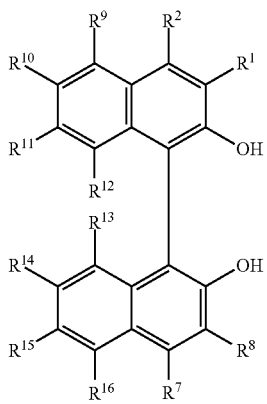

wherein, in the formula, $R^1$, $R^2$, $R^7$, $R^8$, and $R^9$ to $R^{16}$ are each independently a hydrogen atom, a halogen atom, an alkyl group, an alkenyl group, an alkynyl group, an aryl group, an aromatic heterocyclic group, a non-aromatic heterocyclic group, an acyl group, a carboxyl group, an alkoxycarbonyl group, an aryloxycarbonyl group, a carbamoyl group, a hydroxyl group, an alkoxy group, an aryloxy group, a thiol group, an alkylthio group, an arylthio group, an amino group, an alkylamino group, an arylamino group, a cyano group, a nitro group, a silyl group or a siloxy group, which may have a substituent or may be linked to each other to form a ring.

4. The method for producing an optically active alcohol according to claim 3, in which said optically active biphenol compound is the following formula (7), (7)

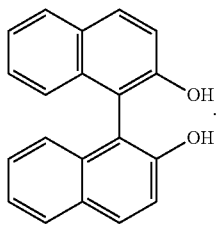

5. The method for producing an optically active alcohol according to claim 1, in which said optically active biphenol compound is represented by the following general formula (8), (8)

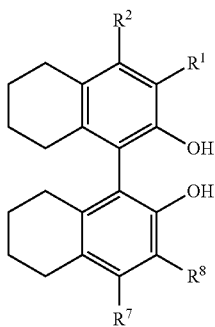

wherein, in the formula, $R^1$, $R^2$, $R^7$ and $R^8$ are each independently a hydrogen atom, a halogen atom, an alkyl group, an alkenyl group, an alkynyl group, an aryl group, an aromatic heterocyclic group, a non-aromatic heterocyclic group, an acyl group, a carboxyl group, an alkoxycarbonyl group, an aryloxycarbonyl group, a carbamoyl group, a hydroxyl group, an alkoxy group, an aryloxy group, a thiol group, an alkylthio group, an arylthio group, an amino group, an alkylamino group, an arylamino group, a cyano group, a nitro group, a silyl group or a siloxy group, which may have a substituent or may be linked to each other to form a ring.

6. The method for producing an optically active alcohol according to claim 5, in which said optically active biphenol compound is the following formula (9), (9)

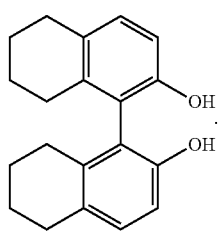

7. The method for producing an optically active alcohol according to claim 1, in which the amount of said ether compound is equal to or more than 10 equivalents, relative to said aromatic magnesium compound.

8. The method for producing an optically active alcohol according to claim 1, in which said ether compound is dioxane.

9. The method for producing an optically active alcohol according to claim 1, in which said titanium compound is represented by the following general formula (10), $$\text{Ti}(OR^a)_m X_{(4-m)} \quad (10)$$

wherein, in the formula, $R^a$ is an alkyl group, an alkenyl group, an aryl group or an acyl group, which may have a substituent; X is a halogen atom; and m is an integer of 0 to 3.

10. The method for producing an optically active alcohol according to claim 1, in which the amount of said optically active biphenol compound is equal to or more than 0.1 mole % and equal to or less than 50 mole %, based on 100 mole % of said carbonyl compound.

11. The method for producing an optically active alcohol according to claim 1, in which the amount of said titanium compound is equal to or more than 50 mole % and equal to or less than 300 mole %, based on 100 mole % of said carbonyl compound.

12. The method for producing an optically active alcohol according to claim 1, in which said carbonyl compound is aldehyde represented by the following general formula (11), (11)

wherein, in the formula, $R^e$ is an alkyl group, an alkenyl group, an alkynyl group, an aryl group, an aromatic heterocyclic group or a non-aromatic heterocyclic group.

13. The method for producing an optically active alcohol according to claim 12, in which said aldehyde is an aromatic aldehyde.

* * * * *